US007078198B1

(12) United States Patent
Vaslin et al.

(10) Patent No.: US 7,078,198 B1
(45) Date of Patent: Jul. 18, 2006

(54) **HETEROPOLYSACCHARIDE PRODUCED BY *PSEUDOMONAS* SP**

(75) Inventors: Sophie Vaslin, Saint-Cloud (FR); Alain Senechal, Charenton (FR); Paule Chevallereau, Melle (FR); Jean-Luc Simon, Lille (FR); Robert Cantiani, Lyons (FR)

(73) Assignee: Rhodia Chimie, Courbevoie (FR)

( * ) Notice: Subject to any disclaimer, the term of this patent is extended or adjusted under 35 U.S.C. 154(b) by 0 days.

(21) Appl. No.: 09/958,673

(22) PCT Filed: Apr. 10, 2000

(86) PCT No.: PCT/FR00/00907

§ 371 (c)(1),
(2), (4) Date: Dec. 3, 2002

(87) PCT Pub. No.: WO00/63412

PCT Pub. Date: Oct. 26, 2000

(30) Foreign Application Priority Data

Apr. 15, 1999 (FR) .................................. 99 04743

(51) Int. Cl.
*C12P 19/04* (2006.01)
*C12N 1/20* (2006.01)
*C08B 37/00* (2006.01)

(52) U.S. Cl. .............. 435/101; 435/253.3; 435/252.34; 536/123; 536/123.1; 536/124; 426/658

(58) Field of Classification Search ................ 435/101, 435/253.3, 252.34; 536/123, 123.1, 124; 426/658
See application file for complete search history.

(56) References Cited

FOREIGN PATENT DOCUMENTS

| | | |
|---|---|---|
| EP | 0 231 585 | 8/1987 |
| EP | 0 410 604 | 1/1991 |
| EP | 0 534 855 | 3/1993 |

OTHER PUBLICATIONS

Fett, F.W. et al., *Applied and Environmental Microbiology*, vol. 61, No. 2, (Feb. 1995), pp. 513-517, XP002125942.
Database FSTA Online, International Food Information Service, Frankfurt/Main, DE; Stabnikova E.V. et al., Database Accession No. 84-3-10-m1181, XP002125943, Abstract.

*Primary Examiner*—Francisco Prats
(74) *Attorney, Agent, or Firm*—Buchanan Ingersoll, P.C.

(57) ABSTRACT

The present invention relates to a heteropolysaccharide (HP) characterized in that it can be obtained by fermentation of a medium comprising at least one strain of Pseudomonas sp I-2054 (or DSM 12295), one of the recombinants thereof or the mutants thereof and a source of carbon which can be assimilated by said strain, one of the recombinants thereof or one of the mutants thereof. The invention also relates to a method for the production and use of said heteropolysaccharide as a thickening agent and/or gelling agent.

27 Claims, No Drawings

HETEROPOLYSACCHARIDE PRODUCED BY *PSEUDOMONAS* SP

The present invention relates to a novel heteropolysaccharide (HP), to a process for preparing it by fermenting a Pseudomonas sp I-2054 (or DSM 12295) strain, to said strain, and to the uses of this heteropolysaccharide as a thickener and/or gelling agent.

In many fields of industry, they are constantly on the lookout for new compounds which feature:

improved rheological properties and are capable of forming gels, increased compatibility with the media in which they are incorporated, great stability within a wide temperature and pH range.

In the case of compounds obtained at the outcome of a bacterial fermentation, it is also important for the compound to have good productivity.

The capacity to gel is of great interest, since such systems are particularly attractive owing to the diversity of fields in which they find applications: some applications require the use of a gel.

Thus, for example, agribusiness provides a wide range of gel products (cream desserts, yogurts, various jellies, ices, etc.), and the pharmaceutical industry uses gels as vehicles for active principles or as thickeners.

In a quite different field, some paints do not drip by virtue of the fact that they possess gel characteristics at rest, whereas they spread easily under the action of the brush (shear-thinning profile).

Aqueous gels are also used as chromatographic supports or else for the development of contact lenses.

Heteropolysaccharides of bacterial origin such as xanthan gum, for example, have already been described and used for their effective rheological properties under extreme temperature and pH conditions. However, these heteropolysaccharides, which are suitable in applications in solution, do not always produce gels.

It is known that the gelling of a medium takes place when a three-dimensional network is formed subsequent to the crosslinking of the components of said medium.

Conventionally, this gelling is brought about by adding additional cations to the medium, especially cations of the alkali metal or alkaline earth metal type (for example calcium and/or magnesium), by switching the pH toward acidic or basic values, by adding another compound, in particular another polysaccharide (for example, the combination of xanthan and carob), or by altering the temperature.

Whatever the application envisaged, the abovementioned gelling conditions may:

harm the stability and the compatibility of the final gel, owing to interactions between the additional cations or the coadditive, which must be introduced in order to obtain the gel, and the other ingredients present in said compositions, or denature the heteropolysaccharide and/or the other ingredients present in said compositions, owing to high temperatures and/or changes in pH.

In the context of the present invention, a "gel" denotes a pseudo-solid (behaving very similarly to a solid) resulting from the at least partial association of heteropolysaccharide chains dispersed in a liquid. Within a stressing frequency range ω, the pseudo-solid gels are generally characterized, with regard to their solid component, by an elastic modulus G'(ω), also called storage modulus, and, with regard to their liquid or viscous component, by a viscous modulus G"(ω), also called loss modulus.

The mechanical values G'(ω) and G"(ω) may be measured using a controlled strain rheometer which operates in oscillatory mode. By way of nonlimiting indication, mention may be made, for example, of a Rheo-Fluid Spectrometer® rheometer.

G' and G" may also be measured on a controlled stress rheometer operating in oscillatory mode. By way of indication, mention may be made, for example, of a CARRIMED® rheometer.

The principle of the measurement consists in determining, firstly, the range of reversible mechanical strain in which the response of the gel to mechanical stress is linear as a function of said strain. Secondly, the gel is subjected to a set value of mechanical strain contained within the linear range determined beforehand. The rheometer then carries out a frequency sweep ω.

The stress response of the gel which is in phase with the strain gives access to the elastic modulus G'(ω). G'(ω) corresponds to the energy stored by the gel in elastic form, and is recoverable.

The stress response of the gel which is out of phase by an angle of 90° with the strain gives access to the viscous modulus G"(ω). G"(ω) corresponds to the energy dissipated by the viscous flow, and is irrecoverable.

A gel is said to be strong or true when, throughout the stress frequency range (ω) swept, the G'/G" ratio is greater than or equal to 10, i.e., when the elasticity of the gel remains high and when the value of G'(ω) is greater than or equal to 10 Pa.

A specific aim of the present invention is to provide heteropolysaccharides which possess very good rheological properties, especially in terms of thickening and pseudoplastic (shear-thinning) properties, and also the capacity to give true gels without the addition of additional cations to the medium and without pH switching, and to do so at temperatures less than or equal to 40° C.

Another aim of the present invention is to provide a heteropolysaccharide having very good rheological properties at low concentrations.

The present invention first provides a heteropolysaccharide (HP) characterized in that it is obtainable by fermenting a medium comprising at least one Pseudomonas sp I-2054 (or DSM 12295) strain, one of its recombinants, or one of its mutants, and a carbon source assimilable by said strain, one of its recombinants, or one of its mutants.

The Pseudomonas sp strain was deposited in accordance with the Treaty of Budapest at the Collection Nationale de Culture des Micro-organismes (CNCM) [National Collection of Micro-organism Cultures], Institut Pasteur, 28, rue du Dr Roux, 75724 Paris Cédex 15, France, on Jul. 22, 1998, where it is publicly accessible under number I-2054. It was also deposited at the Deutsche Sammiung von Mikroorganismen und Zellkulturen GmbH (DSMZ) [German Collection of Micro-organisms and Cell Cultures], Mascheroder Weg 1b. D-38124 Braunschweig, Germany, on Jul. 13, 1998, where it is publicly accessible under number DSM 12295. This strain constitutes one of the subjects of the invention.

Pure culturing of Pseudmonas sp I-2054 (or DSM 12295), which constitutes another aspect of the present invention, may be carried out in a Petri dish incubated at a temperature of between 25° C. and 30° C., and more particularly of between 25° C. and 28° C., for approximately 24 hours.

The nitrogen and carbon sources assimilable by Pseudomonas sp I-2054 (or DSM 12295) may be selected from glucose, fructose, galactose, trehalose, mannose, melobiose, sucrose, raffinose, maltotriose, maltose, lactose, lactulose, methyl-β-galactopyranoside, methyl-α-galactopyranoside, cellobiose, gentobiose, methyl-β-D-glucopyranoside, methyl-α-D-glucopyranoside, esculin, ribose, arabinose, xylose, palatinose, rhamnose, fucose, melezitose, D(+)-arabitol, L(−)-arabitol, xylitol, dulcitol, tagatose, glycerol, myo-innositol, mannitol, maltitol, turanose, sorbitol, adonitol, lyxose, erythritol, D(−)-tartrate, D(+)-malate, L(−)-malate, cis-aconitate, trans-aconitate, 2-keto-D-gluconate, N-acetylglucosamine, quinate, betaine, succinate, fumarate, glycerate and glucosamine.

Among the possible maintenance media for the strain, the maintenance medium of the type Difco MY agar (reference 0712-01-8) is considered to be particularly advantageous. Said Difco MY agar medium has the following composition:

| | |
|---|---|
| bacto-yeast extract | 3 g |
| malt extract | 3 g |
| bacto-peptone | 5 g |
| bacto-dextrose | 10 g |
| bacto-agar | 20 g |

For conserving the strain, it is preferable to provide at least one preculturing step. By a preculturing step is meant a step which consists in developing and multiplying the bacterial strain without producing polysaccharide.

It has been possible to demonstrate that, in general, the heteropolysaccharide (HP) comprises units of glucose and/or its derivatives, galactose and/or its derivatives, mannuronic acid and/or its salts, and acetic acid and/or its salts.

The constituent units of the heteropolysaccharide (HP) are generally present in the following molar proportions, taking, as a reference, galactose as equal to 1:

glucose and/or its derivatives: 0.2–5, mannuronic acid and/or its salts: 0.2–5, acetic acid and/or its salts: 0–10.

More particularly, said units are present in the following molar proportions, taking, as a reference, galactose as equal to 1:

glucose and/or its derivatives: 0.5–4, and preferably 0.8–2, mannuronic acid and/or its salts: 0.5–4, and preferably 0.8–2, acetic acid and/or its salts: 0–8, and preferably 0–6.

The mannuronic and acetic acids may be present in the form of salts. As salts, mention may be made of sodium, potassium, calcium or ammonium salts.

The principle of the methods of analyzing the heteropolysaccharide (HP) which have allowed its empirical formula to be determined as specified above is the determination of the constituent elements (monosaccharides and acids) after hydrolysis of said heteropolysaccharide (HP) and chromatographic assays with internal or external calibration.

Thus, the monosaccharide assay was carried out as follows:

100 mg of heteropolysaccharide (HP) are hydrolyzed in hermetic tubes with 5 ml of molar trifluoroacetic acid at 105° C. from 3 to 6 hours.

This operation is followed by evaporation to dryness and takeup of the dry residue in 5 ml of pyridine containing 15 mg of sorbitol as internal standard; then silylation on 1 ml of pyridine solution with 0.9 ml of hexamethyldisilazane. The silylation is catalyzed by 0.1 ml of trifluoroacetic acid.

The monosaccharides are then assayed by gas chromatography with F.I.D. (Flame Ionization Detection) on a glass capillary column with a length of 25 meters and a diameter of 0.25 mm, packed with methylsilicone phase having a film thickness of 0.14 microns. The carrier gas used is hydrogen, with a flow rate of 2 ml/minute.

The acetic acid is assayed following hydrolysis of 100 mg heteropolysaccharide (HP) with 5 ml of 2 N hydrochloric acid at 105° C. for one hour. Then 5 ml of a 5 mg/ml solution of propionic acid are added as internal standard and the mixture is made up with 15 ml of demineralized water. The assay is carried out by HPLC using a 5 micron C-18 grafted silica column with a length of 250 cm and a diameter of 4.6 mm. The eluent is a 0.02 mol/l aqueous phosphoric acid solution at a flow rate of 1.2 ml/minute. Detection is by refractometry.

The mannuronic acid is assayed by way of the $CO_2$ released by decarboxylation following hot treatment of the gum with hydrochloric acid in accordance with the method described in the Food Chemical Codex, 4th Edition, page 768.

The molar mass by weight is determined by exclusion chromatography on TSK PW 4000 and 6000 columns in series (columns with a length of 30 cm and a diameter of 7 mm), with refractometric detection. The eluent is a 0.1 mol/l sodium nitrate solution. The concentration of the heteropolysaccharide in the eluent is approximately 0.015% by weight. Calibration is carried out using pullulans, which are monodisperse polysaccharides with molar masses of between $5\times10^3$ and $1.6\times10^6$ g/mol extrapolated up to $10^7$ g/mol.

The weight-average molar mass (Mw) is obtained from the mass distribution curve obtained from the chromatogram; it is generally between $1\times10^5$ and $8\times10^6$ g/mol, preferably between approximately $8\times10^5$ and $5\times10^6$ g/mol.

More particularly, (HP) has a weight-average molar mass (Mw) of between approximately $2.5\times10^6$ and $4\times10^6$ g/mol inclusive.

As already mentioned, the (HP) has very good rheological properties in solution, especially in distilled water or mains water.

Thus, it has been found that, for example, 0.5% weight/weight solutions of (HP) in distilled water at 23° C., and at a frequency of 1 Hz, give G' values of between 0.1 and 200 Pa and G" values of between 0.1 and 20 Pa.

(HP) gives strong or true gels when the G' and G" values are advantageously between 20 and 200 Pa for G' and between 0.5 and 15 Pa for G". More advantageously still, G' is between 20 and 150 Pa and G" is between 0.5 and 10 Pa. In one particularly preferred embodiment, the value of G' is approximately 100 Pa and that of G" is approximately 5 Pa (in distilled water).

The (HP) gives the aqueous medium viscosity, which is evaluated by flow rheology. The rheological measurements of flow viscosity are carried out using a controlled stress rheometer or controlled shear rate rheometer, such as, for example, using a viscometer of the RHEOMAT® or CARRIMED® type, respectively.

In both cases, the instrument measures the stress under flow of the HP+water mixture when this mixture is irreversibly strained. The flow viscosity is calculated from the stress.

This instrument therefore makes it possible to quantify the viscosity level at a given shear rate.

The flow viscosity may be more simply evaluated with the aid of a BROOKFIELD® viscometer.

These rheological measurements of (HP) flow viscosity make it possible, moreover, to evaluate the flow threshold of the (HP) solution and/or of the formulation comprising it.

Said threshold represents the force which must be provided in order to destroy the structure of the medium and to force it to flow.

The flow rheology also makes it possible to quantify the ease with which an (HP) solution and/or a formulation comprising it flows when the controlled shearing increases (pseudoplastic or shear-thinning behavior).

It has been found, for example, that 1% weight/weight solutions of HP in distilled water containing 0.5% weight/weight of NaCl, at 23° C., give flow viscosity values, at a shear rate of 0.1 $s^{-1}$, of between 100 and 5 000 Pa·s, and more particularly between 200 and 2 000 Pa·s.

Under similar conditions, at a shear rate of 10 $s^{-1}$, of between 0.5 and 300 Pa·s, and more particularly between 5 and 150 Pa·s.

These flow rheology data are representative of the behavior of the formulation when it is masticated, when it is transferred from one vessel to another, when it is expanded, etc.

The gels obtained by incorporating (—HP) into the medium are self-healing gels; in other words, after shearing, even strong shearing, the "fractured" gels have the ability to reform and to recover their initial properties.

The self-healing ability of the gels obtained from (HP) is evaluated using compression measurements carried out, for example, on an ETIA T2 texturizer composed of a cylindrical measuring body 12.7 mm in diameter, with a penetration rate of 0.05 mm/s, and a penetration height of 15 mm. The plunger is pushed into the gel at the same place a number of times, at different intervals of time, and the compression force is recorded. A determination is made of the slope at the origin, expressed in mN/mm, which is representative of the elasticity of the gel.

For example, a gel is prepared with 0.5% weight/weight of (HP) in distilled water. This gel is then stored for 24 hours before the compression measurements are carried out, either at room temperature (approximately 25° C.) or in the cold, at approximately 6° C.

Compression measurements are carried out at various intervals of time: 0, 5, 15 minutes and 24 hours, with a 5-minute gap between each measurement.

Thus, the slope remains constant is approximately equal to 45±1 mN/mm, irrespective of the measurement time (t=0.5, 15 minutes and 24 hours).

This indicates that the elasticity of the gel is stable and that it has the ability to self-heal a number of times in succession over time, while maintaining the same gel strength.

The present invention also provides a process for preparing the heteropolysaccharide (HP) as defined above.

The preparation process consists firstly in fermenting a medium comprising at least one carbon source assimilable by a Pseudomonas sp I-2054 (or DSM 12295) strain, one of its recombinants or one of its mutants.

Besides said assimilable carbon source, the fermentation medium may also include at least one organic or inorganic nitrogen source and, where appropriate, one or more mineral salts.

The medium is inoculated conventionally with the Pseudomonas I-2054 (or DSM 12295) strain.

As an organic carbon source which is a constituent of the fermentation medium, besides the abovementioned sugars, mention may also be made of sugars such as starch, advantageously hydrolyzed, starch hydrolysates, mixtures of these sugars, and mixtures comprising at least one of these sugars.

More particularly, mention may be made of glucose, sucrose, starch, advantageously hydrolyzed, starch hydrolysates, lactose, mixtures of these sugars, and mixtures comprising at least one of these sugars. Glucose and sucrose are the sugars which are still more preferred.

The carbon source concentration in the fermentation medium may be between 1 and 100 g/l, and preferably between 15 and 60 g/l.

As the organic nitrogen source, mention may be made of casein and caseinates, fish hydrolysates, wheat, corn or soya flours, yeast extracts (baker's yeast, brewer's yeast, lactic yeasts, etc.), corn steep liquor (CSL), urea, and potato proteins.

As inorganic nitrogen sources, mention may be made of ammonium or sodium nitrates, and ammonium phosphates or sulfates.

The fermentation may also take place with a mixture of organic and inorganic nitrogen sources.

The nitrogen source concentration (organic, inorganic, or a mixture of both) in the fermentation medium may be between 1 and 80 g/l, and preferably between 3 and 50 g/l.

The fermentation medium advantageously comprises calcium, alone or, where appropriate, in a mixture with other trace elements, such as iron, manganese and/or magnesium, and also vitamins and nucleotides.

The calcium may be introduced into the medium in the form of a composition or compound which is inorganic or organic, such as CSL, soya flour, or phosphate, nitrate, carbonate or sulfate salts, for example.

The fermentation may be carried out at pressures of between 1 and 4 bar at a temperature of between 25° C. and 35° C., preferably between 25° C. and 30° C., under aerobic conditions.

The pH of the fermentation medium may be between 5 and 9, and preferably between 6 and 8. The pH may be adjusted, where appropriate, with a base such as sodium hydroxide, potassium hydroxide or aqueous ammonia, or with an acid such as sulfuric acid, phosphoric acid, hydrochloric acid or nitric acid.

The fermentation medium, placed in a fermentation tank or container, may be advantageously subjected to agitation. This agitation may be carried out, for example, using a reciprocal shaker, a rotary shaker, a stirring spindle or a column of bubbles. The fermentation time is conventionally longer than 30 hours, but generally between 40 and 100 hours.

The fermentation yields are generally greater than 40%, more particularly between 55 and 75%, and most particularly between 60 and 75% by weight of heteropolysaccharide (HP) produced with respect to the carbon source used.

After fermentation, the heteropolysaccharide (HP) may be separated from the fermentation must by the following steps:

i—the end-of-fermentation must is subjected to a heat treatment at between 80° C. and 120° C. for approximately 10 to 60 minutes, ii—the heteropolysaccharide (HP) is precipitated by means of an at least partly water-miscible organic liquid, iii—the heteropolysaccharide (HP) is separated from the organic liquid.

In step (i), the fermentation must containing the heteropolysaccharide (HP) is advantageously heated at temperatures of between 80° C. and 120° C. for 10 to 60 minutes, and preferably for between 15 and 45 minutes.

The must subjected to the heat treatment above advantageously has a pH of between 6 and 8.

However, this pH may be adjusted if necessary, where appropriate, with a base or an acid.

The latter may be chosen from the bases and acids mentioned above, used for adjusting the pH of the fermentation medium.

According to one preferred variant of the invention, the must obtained from step (i) is held at the same temperature as the temperature of the heat treatment.

In step (ii), the heteropolysaccharide (HP) is recovered from the must obtained in step (i), advantageously by precipitation using an organic liquid which is at least partly water-miscible and in which the heteropolysaccharide (HP) is insoluble or virtually insoluble.

By way of liquids which are suitable according to the present invention, mention may be made of acetone or alcohols containing from 1 to 6 carbon atoms, such as ethanol, propanol, isopropanol, butanol, tert-butanol, or the mixture thereof.

More particularly, the precipitation of (HP) is carried out with isopropanol.

The volume of organic liquid used is generally at least twice that of the volume of must to be treated.

The precipitation of the heteropolysaccharide (HP) with an organic liquid may also be performed in the presence of salts, such as sodium, potassium or calcium sulfates, chlorides or phosphates.

According to one particular embodiment, the precipitation may take place at a temperature of between 40 and 60° C.

The heteropolysaccharide (HP), once precipitated, may then be separated, in step (iii), from the organic liquid.

The separation method is not critical in itself, and may be selected arbitrarily from the usual known separation methods, such as filtration, centrifugation or suction filtering, for example.

The fibers obtained may be optionally dehydrated, for example using acetone or an alcohol such as ethanol, propanol or isopropanol.

The weight of alcohol required to carry out this dehydration operation is generally from 1 to 10 times that of the fibers to be treated.

The dehydrated fibers may undergo further filtration, centrifugation or suction filtering operations.

Where appropriate, the fibers may be dried, ground and/or sieved so as to give a heteropoly-saccharide (HP) powder.

If the desire is to obtain a purer powder, it is possible to treat either the fermentation must or an aqueous solution reconstituted from the powder obtained according to the process described above, using one or more enzymes.

By way of enzymes which may be suitable for this purpose, mention may be made of proteases, mutanases, lipoproteases, cellulases and chitinases.

The enzymatic purification may be combined with or replaced by physical purification processes, such as the various filtration, centrifugation or dialysis methods, or various chromatographic techniques.

The fermentation musts and the reconstituted solutions of heteropolysaccharide (HP), with or without having undergone purification treatment, may be concentrated.

Concentration may be advantageous in certain cases, in particular when the transport costs may thereby be decreased. In addition, the concentrated solutions may be used more rapidly than the heteropolysaccharide (HP) powders.

Concentration may be carried out by all the techniques known to those skilled in the art, in particular evaporation, ultrafiltration or diafiltration.

In the present invention, the heteropoly-saccharide (HP) is advantageously present in the form of a solid of fiber or powder type.

As already mentioned, (HP) has very good rheological properties, and in particular the ability to form true gels. Depending on the fermentation conditions, in particular depending on the components and their concentrations in the culture medium, and/or the precipitation conditions in step (ii) of the process (more particularly whether or not the precipitation takes place in the presence of salts), (HP) has the advantage of being able to be used as a thickener or as a gelling agent, or both.

Thus the present invention provides for the use of the heteropolysaccharide (HP) as described above or as obtained by the process defined above as a thickener and/or gelling agent.

(HP) may be used as a thickener and/or gelling agent, for example, in the petroleum, agrochemical, food, cosmetics, paper and textile industries, and also in paints, contact lenses, glues, inks and household or industrial cleaners.

The amount of heteropolysaccharide (HP) of the invention which may be used in cosmetic compositions depends on the aqueous medium to be thickened and/or to be gelled. This amount may represent from 0.01% to 5% approximately, preferably of the order of from 0.1% to 0.3%, of the weight of the thickened or gelled aqueous medium.

The term "cosmetic composition or formulation" is intended to mean all the cosmetic products or preparations of the type(s) described in annex 1 ("Illustrative list by category of cosmetic products") of European directive no. 76/768/EEC of Jul. 27, 1976, termed cosmetic directive.

The cosmetic compositions may be formulated into a large number of types of products for the skin and/or the hair, such as mousses, gels (in particular styling gels), conditioners, formulations for hair styling or for facilitating the combing of hair, rinsing formulations, hand and body lotions, products which regulate skin moisturization, cleansing milks, makeup remover compositions, creams or lotions for protection against the sun and ultraviolet radiation, beauty creams, antiacne preparations, local analgesics, mascaras, products intended to be applied to the lips or other mucosae, sticks, and other compositions of the same type.

These cosmetic compositions make use of a vehicle, or of a mixture of two or more vehicles, present in said compositions at concentrations of between 0.5% and 99.5% approximately, generally between 5 and 90% approximately.

The choice of appropriate vehicle depends on the nature of the ingredients used and on the destination of said compositions, depending on whether the formulated product is supposed to be left on the surface to which it has been applied (for example, sprays, mousses, tonic lotion or gels) or, on the other hand, rinsed off after use (for example, shampoo, conditioner, rinsing lotions).

The aqueous vehicles present in the cosmetic compositions may also comprise $C_1$–$C_6$ alcohols, in particular methanol, ethanol and isopropanol. They may also comprise another solvent making it possible to solubilize or disperse, in the aqueous medium, the various ingredients used in said compositions.

Said vehicles may thus also comprise a large variety of other solvents, such as acetone, hydrocarbons, halohydrocarbons, linalool, volatile silicones and esters. The various solvents which may be used in the aqueous vehicles may be miscible or immiscible with each other.

When the cosmetic compositions are in the form of sprays, tonic lotions, gels or mousses, the preferential vehicles comprise, besides water, ethanol, volatile derivatives of silicone, and mixtures thereof.

The formulations for aerosol sprays and mousses may also include a propellant capable of generating the products in the form of a mousse or of fine, uniform sprays. By way of examples, mention may be made of trichlorofluoromethane, dichloro-difluoromethane, difluoroethane, dimethyl ether, propane, n-butane or isobutane.

Said aqueous vehicles may take on a large number of forms, in particular those of emulsions, including water-in-oil emulsions, oil-in-water emulsions, and multiple emulsions, the desired viscosity of which may range up to 2 000 000 mPa·s.

Besides the aqueous vehicle, the cosmetic compositions may comprise surfactants, used to disperse, emulsify, solubilize and stabilize various compounds used in particular for their emollient or humectant properties. They may be of anionic, nonionic, cationic, zwitterionic or amphoteric type; by way of examples, mention may be made of:

anionic surfactants in an amount which may range from 3% to 50%, preferably from 5% to 20%, agents such as
- alkyl ester sulfonates
- alkyl sulfates
- alkylamide sulfates
- salts of saturated or unsaturated fatty acids nonionic surfactants in an amount which may range from 0.1% to 30%, preferably from 2% to 10%, agents such as
- polyoxyalkylenated alkylphenols
- glucosamides, glucamides
- glycerolamides derived from N-alkylamines
- polyoxyalkylenated $C_{8-C22}$ aliphatic alcohols
- the products resulting from the condensation of ethylene oxide with a hydrophobic compound resulting from the condensation of propylene oxide with propylene glycol,
- amine oxides
- alkylpolyglycosides and their polyoxyalkylenated derivatives
- amides of $C_{8-C20}$ fatty acids
- ethoxylated fatty acids
- ethoxylated amidoamines, amines, amides amphoteric and zwitterionic surfactants in an amount which may range from 0.1% to 30%, preferably from 1% to 10%, agents such as
- those of betaine type such as
  - betaines
  - sulfobetaines
  - amidoalkylbetaines
  - and sulfobetaines
- alkylsultaines
- products of condensation of fatty acids and of protein hydrolysates,
- cocoamphoacetates and cocoamphodiacetates
- alkylampho-propionates or -dipropionates,
- amphoteric derivatives of alkylpolyamines Conditioners may also be present, in an amount which may range from 0.05% to 5%, preferably from 0.1% to 1%.

Among these, mention may be made of those of synthetic origin which are better known under the name poly-quaternium, such as polyquaterniums −2, −7 and −10, cationic derivatives of polysaccharides, such as hydroxyethyl cocodimonium cellulose, guar hydroxypropyl trimonium chloride, hydroxypropyl guar hydroxypropyl trimonium chloride, nonvolatile derivatives of silicones, such as amodimethicone, cyclomethicones, non-water-soluble and nonvolatile organopolysiloxanes, such as oils, resins or gums such as diphenyldimethicone gums.

The cosmetic compositions may also comprise polymers with film-forming properties which may be used to provide a fixative function. These polymers are generally present at concentrations of between 0.01 and 10%, preferably of between 0.5 and 5%. They are preferably of the type of polyvinylpyrrolidone, copolymers of polyvinylpyrrolidone and methyl methacrylate, copolymers of polyvinylpyrrolidone and vinyl acetate, polyethylene glycol terephthale/-polyethylene glycol copolymers, and sulfonated terephthalic copolyester polymers.

The cosmetic compositions may also comprise polymeric derivatives which exert a protective function, in amounts of the order of 0.01–10%, preferably approximately 0.1–5% by weight; derivatives such as
- cellulose derivatives
- polyvinyl esters grafted onto polyalkylene backbones
- polyvinyl alcohols
- sulfonated terephthalic copolyester polymers
- ethoxylated monoamines or polyamines, polymers of ethoxylated amines The performances of the cosmetic compositions may also be improved by using plasticizers, in an amount which may range from 0.1 to 20% of the formulation, preferably from 1 to 15%. Among these agents, mention may be made of adipates, phthalates, isophthalates, azelates, stearates, silicone copolyols, glycols, castor oil, or mixtures thereof.

It is also possible advantageously to add to these compositions metal-sequestering agents, more particularly those which sequester calcium, such as citrate ions, or polymeric dispersants in an amount of the order of 0.1–7% by weight, in order to control the calcium and magnesium hardness; agents such as
- water-soluble salts of polycarboxylic acids
- polyethylene glycols with molecular masses of the order of 1 000 to 50 000.

It is also possible to incorporate into the cosmetic compositions humectants; mention may be made of glycerol, sorbitol, urea, collagen, gelatin, and emollients which are generally selected from alkylmono-glycerides and alkyldiglycerides, triglycerides such as oils extracted from plants and from vegetables or oils of animal origin or the hydrogenated derivatives thereof, mineral oils or liquid paraffins, diols, fatty esters, and silicones.

To these compounds, it is possible to add, in combination, inorganic particles or powders such as calcium carbonate, inorganic oxides in powder form or in colloidal form such as titanium dioxide, silica, aluminum salts, kaolin, talc, clays and derivatives thereof.

One or more fragrances, colorants and/or opacifiers such as pigments are generally added to these ingredients.

In order to protect the skin and/or hair against attack from the sun and from UV rays, it is possible to add to these formulations sunscreens which are either chemical compounds which strongly absorb UV radiation, or inorganic particles, such as zinc oxide, titanium dioxide or cerium oxides.

Preservatives, such as p-hydroxybenzoic esters, sodium benzoate or any chemical agent which prevents bacterial proliferation or the proliferation of molds and which is conventionally used of the cosmetic compositions, are generally introduced into these compositions at a level of from 0.01 to 3% by weight.

Agents which modify the activity of water and which greatly increase osmotic pressure, such as carbohydrates or salts, may sometimes be used.

The cosmetic composition may also comprise other viscosity-modifying and/or gelling polymers, such as crosslinked polyacrylates, hydrocolloids obtained by fermentation, such as xanthan gum and Rheozan®, cellulose derivatives such as hydroxypropylcellulose or carboxymethylcellulose, guars and the derivatives thereof, etc., used alone or in combination.

The invention provides more particularly for the use of the heteropolysaccharide as a thickener and/or gelling agent in food formulations.

The food formulations to which the heteropolysaccharide (HP) is added are conventionally simple or multiple liquid emulsions, complex gas and liquid emulsions (expanded systems), suspensions of liquids and solids, or any other system combining these possibilities.

In these formulations, the liquid is advantageously water or a liquid comprising water, at least in part.

The food formulations are obtained by implementing the conventional methods for preparing food formulations according to their type. Thus, the (HP), advantageously in the form of a solid of fiber or powder type, is mixed with the other ingredients required for the formulation. The entire mixture may, where appropriate, be homogenized.

The temperature at which the formulation is prepared is not critical in itself. The formulations comprising the (HP) may be sterilized without any damage to their service properties. Another advantage of (HP) is that it is possible to prepare the food formulations without having to heat the ingredients beforehand.

(HP) remains compatible despite the diversity of the food formulations (pH, ionic strength, composition), and substantially retains its properties.

The advantageous rheological properties associated with the heteropolysaccharide (HP) which is the subject of the invention, and also the capacity of the latter to give true gels at temperatures lower than or equal to 40° C., and to do so within a wide pH range, also makes it possible to impart to the formulations in which it is used, alone or in combination with other additives, a texture close to that of formulations comprising exclusively said additives.

The measurable parameters for characterizing the texture of the food formulations are rheological in nature, and consist essentially in measuring the elastic (G') and viscous (G") moduli, and the flow viscosity at a given shear rate. G' and G", and also the viscosity, have been defined above.

The objective of these rheological characteristics is to demonstrate the viscoelastic and/or pseudoplastic behaviors of the formulations, in order to compare them with each other.

(HP), advantageously in the form of a solid of fiber or powder type, has the capacity to impart a shear-thinning profile to the formulation comprising it.

(HP) has, similarly, the capacity to give true gels which are able to self-heal after application of a mechanical stress.

It should be noted that the G' and G" moduli, and also the viscosity, measured for a formulation may be different from those measured for (HP) in distilled water.

In milk-based and set-desserts, such as, for example, flans, it is possible advantageously to replace, at least partially, the usual gelling agents, in particular gelatin, by (HP).

In salty-acid media, such as vinaigrettes, the aqueous medium present may be structured by adding small amounts of (HP).

In the field of confectionery, in particular in jellied candies of the HARIBO® type, it is possible advantageously to replace, at least partially, the gelling agents, such as gelatin for example, by (HP).

In media with high ionic strength, in particular in pigmeat products, (HP) may be added to the carrageenans in order to reinforce the texture, in particular the elastic appearance of sausages, for example.

In formulations intended to be expanded, such as Chantilly creams, toppings or ice creams, (HP) may be used as a thickener and/or gelling agent.

Similarly, (HP) may be used in formulations such as mayonnaises, vegetable mousses or mousses containing proteins, for instance meat or fish mousses, or mousses containing albumin, such as meringues.

As a thickener and/or gelling agent, (HP) may also be part of the composition of yogurts.

In the abovementioned food applications, use is made in general of from 0.01 to 5% by weight, and preferably between 0.05 to 2% by weight, of heteropolysaccharide (HP) relative to the weight of the composition or formulation which comprises it. More preferably still, from 0.1 to 1% by weight of heteropolysaccharide (HP) is used in relation to the weight of the composition or formulation.

It should be noted that the heteropolysaccharide (HP) does not alter the taste of the foods into which it is introduced.

The invention finally provides the food compositions or formulations comprising the heteropolysaccharide (HP) as defined above.

The following examples illustrate the present invention without, however, limiting its scope.

EXAMPLES

Example 1

This example describes the pure culturing of Pseudomonas sp I-2054 (or DSM 12295), and the conditions under which the strain is conserved.

Pure culturing of Pseudomonas sp I-2054 (or DSM 12295):

The medium for maintaining the Pseudomonas sp I-2054 (or DSM 12295) strain is Difco MY agar medium (reference 0712-01-8). The composition of this medium, already made up, is:

| | |
|---|---|
| bacto-yeast extract | 3 g |
| malt extract | 3 g |
| bacto-peptone | 5 g |
| bacto-dextrose | 10 g |
| bacto-agar | 20 g |

21 g of this medium are diluted in one liter of distilled water. After dissolution, the medium is sterilized in an autoclave for 15 minutes at 121° C. The medium is then distributed into Petri dishes.

Culturing is carried out on Petri dishes incubated at between 25° C. and 30° C., preferably between 25° C. and 28° C., for a minimum of 24 hours.

Preculturing—Conservation:

The strain is then conserved in the form of a tube frozen at −196° C. by the process of liquid nitrogen freezing (LNF).

For liquid nitrogen freezing (LNF) a preculture is prepared on PYG10 medium having the following composition:

| malt extract | 3 g | (obtained from Oxoïd) |
|---|---|---|
| yeast extract | 3 g | (Oxoïd) |
| soya peptone | 5 g | (Oxoïd) |
| glucose | 10 g | (obtained from Prolabo) |
| mineral water qs | 1 l. | |

For preparing the medium, all the ingredients are dispersed in the mineral water. The pH is adjusted to 6.5 with 10% $H_2SO_4$. The medium is sterilized for 20 minutes at 120° C. in an autoclave.

After incubation for 24 hours at 28° C. on a rotary shaker at 220 rpm and amplitude=50 mm, 10% by volume of pure sterile glycerol are added to the culture. The culture is then distributed into cryotubes with capacities ranging from 1 ml to 10 ml, preferably from 2 ml to 4 ml.

These tubes are conserved in liquid nitrogen.

Example 2

This example describes the preparation and production of the heteropolysaccharide according to two fermentation processes, one with an organic nitrogen source and the other with an inorganic nitrogen source.

In this example, two "preculturing" steps are involved. These steps take place in 500 ml Erlenmeyer flasks, which corresponds to 100 ml of medium.

The production step, which corresponds to the step during which the bacterial strain produces the polysaccharide, takes place in a 20 liter fermenter having a useful capacity of 15 liters.

The agitation conditions of the rotary shaker are: speed=220 rpm and amplitude=50 mm.

Preculturing Step 1:

Preculturing step 1 is carried out with a PYG 10 medium of the following composition:

| malt extract | 3 g | (Oxoïd) |
|---|---|---|
| yeast extract | 3 g | (Oxoïd) |
| bacto-peptone | 5 g | (Oxoïd) |
| glucose | 10 g | (Prolabo) |
| distilled water qs | 1 l. | |

All the ingredients are dispersed in a quantity of distilled water sufficient for 1 l. The pH is adjusted, before sterilization, to 6.5 with 10% $H_2SO_4$. The medium is sterilized for 20 minutes at 120° C. in an autoclave.

After sterilization and before inoculation with the cryotube (qs), the pH is at 7.33.

Each Erlenmeyer flask is seeded with a sufficient quantity of the LNF.

After incubation for 24 hours at 28° C. on a rotary shaker (220 rpm, A=50 mm), the medium has the following characteristics:

pH=6.50 viscosity<10 mPa·s the population read on MY agar (Difco medium, reference 0712-01-8) after 72 hours at 28° C.

$=1.7\times10^5$ cfu/ml.

After incubation for 24 hours, preculture 1 is used to seed preculture 2.

Preculturing Step 2:

Preculturing step 2 is carried out with a medium of the following composition:

| yeast extract | 4 g | (Oxoïd) |
|---|---|---|
| $MgSO_4.7H_2O$ | 0.8 g | (Prolabo) |
| $FeSO_4.7H_2O$ | 0.01 g | (Prolabo) |
| $MnSO_4.H_2O$ | 5 ppm $Mn^{2+}$ | (Prolabo) |
| $K_2HPO_4$ | 4 g | (Prolabo) |
| or $Na_2HPO_4$ | 3 g | (Prolabo) |
| glucose | 10 g | (Prolabo) |
| deionized water qs | 1 l | |

A 100 g/l glucose solution is prepared in distilled water and then sterilized at natural pH for 15 minutes at 121° C.

The remainder of the ingredients is dispersed in a quantity of deionized water sufficient for 900 ml, and then adjusted to pH 6.8 before sterilization for 15 minutes at 121° C.

After sterilization, 10 ml of the glucose solution are added to each Erlenmeyer flask.

After sterilization and before inoculation, the pH is 6.88.

Each Erlenmeyer flask is inoculated with the quantity sufficient for preculture 1.

After incubation for 24 hours at 28° C. on a rotary shaker (220 rpm, A=50 mm), the medium has the following characteristics:

pH=6.82 viscosity=50–100 mPa·s the population read on MY agar (Difco medium, reference 0712-01-8) after 72 hours at 28° C.

$=1.6\times10^9$ cfu/ml.

After incubation for 24 hours, preculture 2 is used to seed the two fermentation media (fermenters 1 and 2) in the production step.

Production Step:

The final step is the heteropolysaccharide (HP) production step.

The medium of fermenter 1 has the following composition:

| glucose | 20 g | (Prolabo) |
|---|---|---|
| CSL (corn steep liquor) | 6 g | (Prolabo) |
| $MgSO_4.7H_2O$ | 0.8 g | (Prolabo) |
| $MnSO_4.H_2O$ | 5 ppm $Mn^{2+}$ | (Prolabo) |
| $K_2HPO_4$ | 1 g | (Prolabo) |
| antifoam | 0.2 ml | |
| deionized water qs | 1 l | |

Glucose $\Rightarrow$ the sufficient number of grams of glucose are dissolved in a quantity of deionized water sufficient for 3 l. The pH is lowered to 5 with 10% $H_2SO_4$. The solution is sterilized in a Mariotte flask for 30 minutes at 120° C. in an autoclave. Nitrogen+salts $\Rightarrow$ the sufficient number of grams of corn steep liquor (CSL), 15 g of $K_2HPO_4$, 12 g of $MgSO_4 \cdot 7H_2O$, 23 ml of a 10 g/l solution of $MnSO_4 \cdot H_2O$ and 3 ml of antifoam are dissolved in a quantity of deionized water sufficient for 7 l. The pH is adjusted to 6.5 with 10% $H_2SO_4$. This mixture is sterilized in situ for 30 minutes at 120° C. 1 N sodium hydroxide $\Rightarrow$ 40 g of NaOH pellets are dissolved in a quantity of distilled water sufficient for 1 l. The solution is sterilized in a Mariotte flask for 30 minutes at 120° C. in an autoclave.

When all the ingredients are at 28° C., they are mixed in the fermenter. The fermenter is then inoculated with the qs of preculture 2.

The fermentation conditions in fermenter 1 are as follows:

Agitation ⇛200 rpm from 0 to 20 hours old, then 400 rpm until the end of fermentation.

Aeration ⇛400 l/h from 0 to 18 hours, and then 825 l/h from 24 hours until the end of fermentation.

The temperature is regulated at 28° C.

The pH is regulated at 6.8 with 1 N NaOH.

The pressure is atmospheric pressure.

The medium of fermenter 2 has the following composition:

| | | |
|---|---|---|
| $NaNO_3$ | 1.2 g | (Prolabo) |
| $NH_4NO_3$ | 0.25 g | (Prolabo) |
| $CaSO_4.2H_2O$ | 0.3 g | (Prolabo) |
| $MgSO_4.7H_2O$ | 0.8 g | (Prolabo) |
| $MnSO_4.H_2O$ | 5 ppm $Mn^{2+}$ | (Prolabo) |
| $FeSO_4.7H_2O$ | 0.01 g | (Prolabo) |
| $Na_2HPO_4$ | 3 g | (Prolabo) |
| glucose | 45 g | (Prolabo) |
| antifoam | 0.2 ml | |
| demineralized water qs | 1 l | |

Glucose ⇛the sufficient number of grams of glucose are dissolved in a quantity of deionized water sufficient for 3 l. The pH is adjusted to 5 with 10% $H_2SO_4$. The solution is sterilized in a Mariotte flask for 30 minutes at 120° C. in an autoclave.

Nitrogen+salts ⇛18 g of $NaNO_3$, 3.75 g of $NH_4NO_3$, 4.5 g of $CaSO_4·2H_2O$, 23 ml of a 10 g/l solution of $MnSO_4·H_2O$, 12 g of $MgSO_4·7H_2O$, 75 ml of a 2 g/l solution of $FeSO_4·7H_2O$, 4.5 g of $Na_2HPO_4$ and 3 ml of antifoam are dissolved in a quantity of demineralized water sufficient for 7 l. The pH of this solution is adjusted to 6 with 10% $H_2SO_4$. This mixture is sterilized in situ for 30 minutes at 120° C. 1 N sodium hydroxide ⇛40 g of NaOH pellets are dissolved in a quantity of distilled water sufficient for 1 l. The solution is sterilized in a Mariotte flask for 30 minutes at 120° C. in an autoclave.

When all the ingredients are at 28° C., they are mixed in the fermenter. The fermenter is then inoculated with the sufficient quantity of preculture 2.

The fermentation conditions in fermenter 2 are as follows:

Agitation ⇛200 rpm from 0 to 20 hours old, then 400 rpm until the end of fermentation.

Aeration ⇛400 l/h from 0 to 24 hours, and then 825 l/h from 24 hours until the end of fermentation.

The temperature is regulated at 28° C.

The pH is regulated at 6.8 with 1 N NaOH.

The pressure is atmospheric pressure.

Fermentation Results:

Depending on the culture medium studied, the fermentation times range from 60 to 115 hours, the solids which may be precipitated with isopropanol range from 10 to 18 g/kg and the weight yield with respect to the carbon source used ranges from 44 to 70%.

Extraction and Purification:

The end-of-fermentation must is stabilized with 10% (weight/weight) of pure IPA. It is then heat-treated at 100–110° C. for 20 minutes at pH 7. The pH, during the heat treatment, does not vary.

On emergence from the heat treatment, the must is extracted while hot (temperature>70° C.).

The precipitation conditions are:

1.7 kg of hot must in 4.5 kg of pure IPA (at approximately 50° C.).

After precipitation, the fibers are chopped up and then washed and dehydrated with IPA having a titer of 78%.

The fibers are then dried in a ventilated oven at approximately 85° C. until a product is obtained which has a moisture content of approximately 10% by weight.

The fibers are then ground and sieved.

The analysis of the units of the heteropolysaccharide obtained in the medium of fermenter 1 (organic medium) is as follows in molar proportions (percentage by mass):

| | | |
|---|---|---|
| galactose | 1 | (13%) |
| glucose | 1.08 | (14%) |
| mannuronic acid | 1.1 | (17%) |
| acetic acid | 4.3 | (18.6%) |

The analysis of the units of the heteropolysaccharide obtained in the medium of fermenter 2 (inorganic medium) is as follows (percentage by mass):

| | |
|---|---|
| galactose | (22.5%) |
| glucose | (21.7%) |
| mannuronic acid | (26%) |
| acetic acid | (31%) |

Example 3

The subject of this example is the use of (HP) obtained in example 2 in a food formulation for topping.

In the examples which will follow, the flow viscosities, expressed in mPa·s, were measured using a BROOKFIELD RVT 20-2 viscometer at room temperature.

The values of the elastic moduli, expressed in Pa, were produced using a CARRIMED CSL 100 controlled stress rheometer. They were measured in an oscillatory system—frequency from 0.01 to 10 Hz.

The measurements of degree of expansion, expressed in %, were carried out as follows:

the mousse is introduced into a beaker of known volume (V) and of known mass, the beaker is given three sharp taps, and the mousse is leveled;

the beaker is weighed in order to determine the mass (M) of mousse that it contains;

the degree of expansion=[M(g)/V(ml)]×100

Two formulations are prepared:

formulation 3.1: comprising the heteropolysaccharide (HP) according to the invention, formulation 3.2 (comparative): comprising sodium caseinate and sodium alginate.

The compositions of the formulations are summarized in table I.

TABLE I

| Components | Formulation 3.1 (% by weight) | Formulation 3.2 (% by weight) |
|---|---|---|
| Oily phase | | |
| Hydrogenated palm oil | 7.6 | 7.6 |
| Monodiglyceride acetic ester | 0.76 | 0.76 |
| Monodiglyceride lactic ester | 0.76 | 0.76 |
| Aqueous phase | | |
| Sugar | 8.35 | 8.35 |
| Powdered skimmed milk | 7.44 | 7.44 |
| Maltodextrin (Glucidex ® 19) | 4.6 | 4.6 |
| Sodium caseinate | — | 1.5 |
| Sodium alginate | — | 0.02 |
| Heteropoly-saccharide (HP) | 0.5 | — |
| Water | qs 100 | qs 100 |

Aqueous Phase:

In a beaker equipped with a deflocculating paddle, the amount of water required is weighed out and the mixture of powders described in the table above is dispersed with vigorous stirring (500 rpm).

The stirring is maintained for 5 minutes after said powders have been introduced.

Oily Phase:

In a beaker, the fatty substance and the emulsifiers are heated, in a water bath, to 70° C.

The oily phase is then added to the aqueous phase with stirring at 1 000 rpm.

The stirring is maintained for 5 minutes after the oily phase has been introduced. During this operation, the water evaporation is compensated.

The entire mixture is then homogenized using an Ultra-Turrax for 2 minutes at 20 000 rpm.

The mixture is cooled to a temperature lower than 10° C., before carrying out the expansion. This takes place using a laboratory mixer of the KENWOOD CHEF type, at maximum speed for 3 minutes at a temperature close to 5° C.

The results are collated in table II.

TABLE II

| | Formulation 3.1 | Formulation 3.2 |
|---|---|---|
| Viscosity before expansion (mPa · s) | 1 500 | 1 700 |
| Degree of expansion (%) | 350 | 250 |
| G' measured at 1 Hz (Pa) | 1 800 | 1 600 |
| G" measured at 1 Hz (Pa) | 300 | 400 |

These results show that formulation 3.1, which uses the (HP) according to the invention, has a viscosity lower than that of comparative formulation 3.2 and, because of this, is easier to expand.

In addition, formulation 3.1 (according to the invention) is firstly more gelled (higher G' at high frequency), and has an improved degree of expansion.

The invention claimed is:

1. A heteropolysaccharide (HP) which is obtained by fermenting a medium comprising at least one Pseudomonas sp 1-2054 (or DSM 12295) strain, and a carbon source assimilable by said strain.

2. The heteropolysaccharide (HP) as claimed in claim 1, which comprises units of glucose, galactose, and/or their derivatives, mannuronic acid, acetic acid, and/or their salts.

3. The heteropolysaccharide (HP) as claimed in claim 2, wherein said units are present in the following molar proportions, taking, as a reference, galactose as equal to 1:

glucose and/or its derivatives: 0.2–5, mannuronic acid and/or its salts: 0.2–5, acetic acid and/or its salts: 0–10.

4. The heteropolysaccharide (HP) as claimed in claim 1, wherein said units are present in the following molar proportions, taking, as a reference, galactose as equal to 1:

glucose and/or its derivatives: 0.5–4, mannuronic acid and/or its salts: 0.5–4, acetic acid and/or its salts: 0–8.

5. The heteropolysaccharide (HP) as claimed in claim 1, wherein mannuronic and acetic acid are present in the form of salts.

6. The heteropolysaccharide (HP) as claimed in claim 1, which has a weight-average molar mass (Mw) of between $1\times10^5$ and $8\times10^6$ g/mol.

7. The heteropolysaccharide (HP) as claimed in claim 1, which has a weight-average molar mass (Mw) of between approximately $2.5\times10^6$ and $4\times10^6$ g/mol inclusive.

8. The heteropolysaccharide (HP) as claimed in claim 1, wherein 0.5% weight/weight solutions of said heteropolysaccharide (HP) in distilled water at 23° C., and at a frequency of 1 Hz, give G' values of between 0.1 and 200 Pa and G" values of between 0.1 and 20 Pa.

9. The heteropolysaccharide (HP) as claimed in claim 1, wherein 0.5% weight/weight solutions of said heteropolysaccharide (HP) in distilled water at 23° C., and at a frequency of 1 Hz, give G' values of between 20 and 200 Pa and G" values of between 0.5 and 15 Pa.

10. The heteropolysaccharide (HP) as claimed in claim 1, wherein 1% weight/weight solutions of said HP in distilled water containing 0.5% weight/weight of NaCl, at 23° C., give flow viscosity values at a shear rate of 0.1 $s^{-1}$ of between 100 and 5 000 Pa·s, and more particularly between 200 and 2 000 Pa·s.

11. The heteropolysaccharide (HP) as claimed in claim 1, wherein 1% weight/weight solutions of said HP in distilled water containing 0.5% weight/weight of NaCl, at 23° C., give flow viscosity values, at a shear rate of 10 $s^{-1}$, of between 0.5 and 300 Pa·s.

12. A process for preparing the heteropolysaccharide (HP) as defined in claim 1, wherein the heteropolysaccharide (HP) is separated from the fermentation must by the following steps:

i—the end-of-fermentation must is subjected to a heat treatment at between 80° C. and 120° C. for approximately 10 to 60 minutes, ii—said heteropolysaccharide (HP) is precipitated by means of an at least partly water-miscible organic liquid, iii—the heteropolysaccharide (HP) is separated from the organic liquid.

13. The process as claimed in claim 12, wherein in step (i) the must subjected to the heat treatment has a pH of between 6 and 8.

14. The process as claimed in claim 12, wherein the must obtained from step (i) is held at the same temperature as the temperature of the heat treatment.

15. The process as claimed in claim 12, wherein in step (ii) the precipitation of the heteropolysaccharide (HP) with an organic liquid is performed in the presence of salts, comprising sodium, potassium or calcium sulfates, chlorides or phosphates.

16. The process as claimed in claim 12, wherein in step (ii) precipitation takes place at a temperature of between 40 and 60° C.

17. An isolated Pseudomonas sp strain deposited at the CNCM under number I-2054 and also at DSMZ under number DSM 12295.

18. A pure culture of Pseudomonas sp I-2054 (or DSM 12295).

19. A thickener and/or gelling agent comprising the heteropolysaccharide (HP) as claimed in claim 1.

20. A food formulation comprising the heteropolysaccharide (HP) as claimed in claim 1 in amounts of between 0.01 to 5% by weight as a thickener and/or gelling agent.

21. A method to obtain gels without adding additional cations to the medium comprising using the heteropolysaccharide (HP) as claimed in claim 1.

22. A composition or formulation comprising the heteropolysaccharide (HP) as described in claim 1 and a carrier.

23. A heteropolysaccharide (HP) which is obtained by fermenting a medium comprising at least one recombinant or one mutant of Pseudomonas sp I-2054 (or DSM 12295) strain, and a carbon source assimilable by said recombinant or said mutant, which comprises units of glucose, galactose, and/or their derivatives, mannuronic acid, acetic acid, and/or their salts, wherein said units are present in the following molar proportions, taking, as a reference, galactose as equal to 1:

glucose and/or its derivatives: 0.2–5, mannuronic acid and/or its salts: 0.2–5, acetic acid and/or its salts: 0–10, which has a weight-average molar mass (Mw) of between approximately $1\times10^5$ and $8\times10^6$ g/mol inclusive.

24. A thickener and/or gelling agent comprising the heteropolysaccharide (HP) as claimed in claim 23.

25. A food formulation comprising the heteropolysaccharide (HP) as claimed in claim 23 in amounts of between 0.01 to 5% by weight as a thickener and/or gelling agent.

26. A method to obtain gels without adding additional cations to the medium comprising using the heteropolysaccharide (HP) as claimed in claim 23.

27. A composition or formulation comprising the heteropolysaccharide (HP) as described in claim 23 and a carrier.

* * * * *